United States Patent
Langendijk et al.

(10) Patent No.: US 12,186,289 B2
(45) Date of Patent: Jan. 7, 2025

(54) COMPOSITIONS FOR FEEDING A PREGNANT ANIMAL

(71) Applicant: Nutreco IP Assets B.V., Boxmeer (NL)

(72) Inventors: Pieter Langendijk, Boxmeer (NL); Theodorus Antonius Theresia Gerardus Van Kempen, Boxmeer (NL)

(73) Assignee: Nutreco IP Assets B.V., Boxmeer (NL)

( * ) Notice: Subject to any disclaimer, the term of this patent is extended or adjusted under 35 U.S.C. 154(b) by 790 days.

(21) Appl. No.: 17/324,745

(22) Filed: May 19, 2021

(65) Prior Publication Data

US 2021/0275481 A1 Sep. 9, 2021

Related U.S. Application Data

(63) Continuation of application No. PCT/EP2019/081842, filed on Nov. 19, 2019.

(30) Foreign Application Priority Data

Nov. 20, 2018 (EP) ..................................... 18207271

(51) Int. Cl.
*A61K 31/198* (2006.01)
*A23K 20/105* (2016.01)
*A23K 50/30* (2016.01)
*A61K 9/00* (2006.01)
*A61K 31/19* (2006.01)

(52) U.S. Cl.
CPC .......... *A61K 31/198* (2013.01); *A23K 20/105* (2016.05); *A23K 50/30* (2016.05); *A61K 9/0056* (2013.01); *A61K 31/19* (2013.01)

(58) Field of Classification Search
CPC .... A61K 31/198; A61K 9/0056; A61K 31/19; A23K 20/105; A23K 50/30; A23K 20/142; Y02P 60/87; Y02P 60/50
See application file for complete search history.

(56) References Cited

FOREIGN PATENT DOCUMENTS

| CN | 103315156 A | 9/2013 | |
|---|---|---|---|
| DE | 10326346 A1 | 12/2004 | |
| EP | 1 228 698 A1 | 8/2002 | |
| WO | WO-96/32850 | 10/1996 | |
| WO | WO-9632850 A1 * | 10/1996 | ........... A23K 20/105 |

OTHER PUBLICATIONS

Wang Haifeng et al: "Sorbic acid: effects on performance and serum biochemical indices of lactating sows and suckling piglets ", Chinese Journal of Animal Nutrition, vol. 25, No. 1, 2013 , pp. 118-125.*
Ramis G; Evangelista JNB; Quereda JJ; et al: "Use of betaine in gilts and sows during lactation: effects on milk quality, reproductive parameters, and piglet performance", Journal of Swine Health and Production, vol. 19, No. 4, 2011, pp. 226-232.*
International Search Report and Written Opinion for PCT/EP2019/081842 dated Dec. 13, 2019.
Kashyap et al., "Ursolic acid (UA): A metabolite with promising therapeutic potential." Life Sciences, vol. 146, 2016, pp. 201-213.
Kirchgessner et al., "Zur nutritiven Wirkung von Sorbinsaure in der Ferkelaufzucht." J. Anim. Physiol. a. Anim. Nutr., vol. 74, 1995, pp. 235-242.
Luo et al., "Sorbic acid improves growth performance and regulates IGF system gene expression in swine." Journal of Animal Science, 2011, pp. 1-29.
Ramis et al., "Use of betaine in gilts and sows during lactation: effects on milk quality, reproductive parameters, and piglet performance." Journal of Swine Health and Production. vol. 19 No. 4, 2011, pp. 226-232.
Theil et al., "Mechanistic model to predict colostrum intake based on deuterium oxide dilution technique data and impact of gestation and prefarrowing diets on piglet intake and sow yield of colostrum", J. Anim. Sci., 2014, vol. 92, pp. 5507-5519.
Wang Haifeng et al., Chinese Journal of Animal Nutrition, vol. 25(1), 2013, pp. 118-125.

* cited by examiner

*Primary Examiner* — Deborah D Carr
(74) *Attorney, Agent, or Firm* — Sunit Talapatra; Foley & Lardner LLP

(57) ABSTRACT

The present invention pertains to the field of maximizing performance of animals, particularly of pregnant animals and their offspring, particularly of pregnant sows and their offspring. Particularly the present invention is in the field of increasing the colostrum production of a sow, increasing average daily gain of the offspring, and/or improving neonatal survival of the offspring.

21 Claims, No Drawings

COMPOSITIONS FOR FEEDING A PREGNANT ANIMAL

CROSS-REFERENCE TO RELATED APPLICATIONS

This application is a continuation of International Application No. PCT/EP2019/081842, filed Nov. 19, 2019, which claims the benefit of and priority to European Application No. 18207271.0, filed Nov. 20, 2018, both of which are hereby incorporated by reference herein in their entireties.

FIELD OF THE INVENTION

The present invention pertains to the field of maximizing performance of animals, particularly of pregnant animals and their offspring, particularly of pregnant sows and their offspring. Particularly the present invention is in the field of increasing the colostrum production of a sow, increasing average daily gain of the offspring, and/or improving neonatal survival of the offspring.

BACKGROUND OF THE INVENTION

Maximizing the performance of pregnant animals and their offspring has been a major objective of nutritionists for a long time. One important aspect of maximizing reproductive performance is to optimize colostrum production in a pregnant animal. Colostrum is produced by the mammary glands of the animal, which means that the quality and degree of development of the mammary glands is of great importance for the colostrum yield. It is believed that the amount of colostrum consumed by the offspring at the very beginning of life has a positive impact on its performance during the rest of life.

Wang HaiFeng et al. (Chinese Journal of Animal Nutrition, 25(1), pp. 118-125, 2013) described the effects of supplementation of sorbic acid in sow diets on performance of lactating sows and piglets. Performance and serum parameters were measured in suckling piglets between day 1 and 7 and between day 1 and 21 of lactation.

Ramis, G. et al. (Journal of Swine Health and Production, 19(4), pp. 226-232, 2011) described the effects of betaine inclusion in the feed of gilts and multiparous sows and their litters. Betaine was administered from 5 days before the expected farrowing date until the end of the lactation period.

WO96/32850 describes betaine administration in sows in a lactation diet. When betaine level in the diet was increased a reduction in piglet growth rate was observed.

It is an object of the present invention to provide a composition, suitable for increasing colostrum production of a sow, increasing average daily gain of piglets and/or improving neonatal survival of the offspring, a method of feeding such composition to a pregnant animal, preferably a sow, a method of producing such composition, and use of the composition for increasing the colostrum production of a sow, increasing average daily gain of the offspring, and/or improving neonatal survival of the offspring.

SUMMARY OF THE INVENTION

Without wishing to be bound by theory, it is believed that use of the composition of the invention increases mammary gland tissue mass during mammary gland development, in order to effectively increase colostrum production of a sow, to increase average daily gain of the offspring, and/or to improve neonatal survival of the offspring.

In a first aspect, the present invention relates to a method of feeding a pregnant animal, preferably a pregnant mammal, more preferably a pregnant monogastric mammal, most preferably a pregnant sow, comprising administering a composition comprising sorbic acid or an ester or salt thereof and betaine to the pregnant animal, wherein the dosage of sorbic acid or an ester or salt thereof is in a range of 0.02-100 grams per day, and the dosage of betaine is in a range of 0.02-100 grams per day.

In an embodiment, the composition further comprises ursolic acid or an ester or salt thereof.

In an embodiment, the dosage of ursolic acid or an ester or salt thereof is in a range of 0.02-100 grams per day.

In an embodiment, the mammal is a monogastric mammal, preferably a sow.

In another aspect, the present invention relates to a method of producing a composition for a pregnant mammal, comprising mixing sorbic acid or an ester or salt thereof and betaine, with one or more feed components or one or more feed additives or water, to produce the composition, wherein the amount of sorbic acid or an ester or salt thereof in the composition is intended to provide a dosage in a range of 0.02-100 grams per day, and the amount of betaine in the composition is intended to provide a dosage in a range of 0.02-100 grams per day.

In an embodiment, the method comprises an additional step of mixing ursolic acid or an ester or salt thereof, with one or more feed components or one or more feed additives or water, to produce the composition.

In an embodiment, the amount of ursolic acid or an ester or salt thereof in the composition is intended to provide a dosage in a range of 0.02-100 grams per day.

In an embodiment, the composition is selected from a group consisting of a top dress formulation, an animal feed, a premix or supplement and an animal drinking water.

The composition may be administered to the pregnant mammal in a period from about 45 days prior to parturition until parturition, preferably from about 40 days prior to parturition until parturition, more preferably from about 35 days prior to parturition until parturition.

In another aspect, the present invention relates to the use of a composition comprising sorbic acid or an ester or salt thereof and betaine, in a diet for a pregnant mammal, preferably a sow, wherein the dosage of sorbic acid or an ester or salt thereof is in a range of 0.02-100 grams per day, and the dosage of betaine is in a range of 0.02-100 grams per day.

In an embodiment, the composition further comprises ursolic acid or an ester or salt thereof.

In an embodiment, the dosage of ursolic acid or an ester or salt thereof is in a range of 0.02-100 grams per day.

In a further aspect, the present invention relates to the use of a composition comprising sorbic acid or an ester or salt thereof and betaine, for increasing the colostrum production.

In a further aspect, the present invention relates to the use of a composition comprising sorbic acid or an ester or salt thereof and betaine, for increasing average daily gain of offspring of a mammal.

In a further aspect, the present invention relates to a composition comprising sorbic acid or an ester or salt thereof and betaine, for use in improving neonatal survival of offspring of a mammal.

In a further aspect, the present invention relates to a composition comprising sorbic acid or an ester or salt thereof and betaine, for use in increasing the number of offspring of a mammal that reach the age of three weeks.

In an embodiment, the composition further comprises ursolic acid or an ester or salt thereof.

In an embodiment, the composition is selected from the group consisting of a top dress formulation, an animal feed, a premix or supplement and an animal drinking water.

In an aspect, to present invention relates to a supplement, premix or top-dress, suitable for feeding a mammal, comprising sorbic acid or an ester or salt thereof and betaine.

In an embodiment, the supplement, premix or top-dress further comprises ursolic acid or an ester or salt thereof.

In an aspect, the present invention relates to an animal feed, comprising sorbic acid or an ester or salt thereof and betaine.

In an embodiment, the dosage of sorbic acid or an ester or salt thereof is in a range of 0.02-100 grams per kilogram animal feed, and the dosage of betaine is in a range of 0.02-100 grams per kilogram animal feed.

In an embodiment, the animal feed further comprises ursolic acid or an ester or salt thereof.

In an embodiment, the dosage of ursolic acid or an ester or salt thereof is in a range of 0.02-100 grams per kilogram animal feed.

In another aspect, the present invention relates to an animal drinking water, comprising sorbic acid or an ester or salt thereof and betaine, wherein the dosage of sorbic acid or an ester or salt thereof is in a range of 0.02-100 grams per liter animal drinking water, and the dosage of betaine is in a range of 0.02-100 grams per liter animal drinking water.

In an embodiment, the animal drinking water further comprises ursolic acid or an ester or salt thereof.

In an embodiment, the dosage of ursolic acid or an ester or salt thereof is in a range of 0.01-100 grams per liter animal drinking water.

DETAILED DESCRIPTION OF THE INVENTION

General Definitions

In the following description and examples, a number of terms are used. In order to provide a clear and consistent understanding of the specification and claims, including the scope to be given to such terms, the following definitions are provided. Unless otherwise defined herein, all technical and scientific terms used have the same meaning as commonly understood by one of ordinary skill in the art to which this invention belongs. The disclosures of all publications, patent applications, patents and other references cited herein are incorporated herein in their entirety by reference.

The term 'pregnant' or 'pregnancy', also known as 'gestation', as used herein refers to the period of time between conception and parturition, wherein the embryo or fetus is developing in the uterus. The duration of the gestation strongly varies from species to species. Smaller animals usually have shorter periods of gestation than larger animals. In pigs the gestation normally lasts for about 115 days, but there can be some variability from case to case. Gestation can be divided into different phases like fertilization at the very beginning, placental formation, fetal development and major fetal growth at the end, before parturition. Another important development during gestation is mammary gland development, which in pigs typically takes place between around day 80 (around 35 days before parturition) and parturition. During that period of time the mammary gland will develop and get ready for the energy demanding lactation phase.

The term 'parturition', also known as 'farrowing', as used herein refers to the process of giving birth. In pigs this process typically ranges from three to eight hours and piglets are usually delivered every 10 to 20 minutes but there is a wide variation. Between the first and second piglet there can be a gap of up to an hour. The process of parturition is activated by the piglets when they reach the final stage of maturity and signal the uterus produce prostaglandins which are circulated to the ovary and cause luteolysis. This finally results in termination of the pregnancy and activation of parturition.

The term 'neonatal survival', as used herein refers to the survival of newborn animals within ten days after birth. It is the opposite of neonatal mortality or neonatal death, which is the phenomenon where offspring dies shortly after birth, typically within ten days after birth.

The term 'pre-wean survival', as used herein refers to the survival of newborn animals until weaning, which is within about 3 to 4 weeks after birth. It is the opposite of pre-wean mortality or pre-wean death, which is the phenomenon where offspring dies after birth, typically within 3 to 4 weeks after birth. Pre-wean survival means that the animal survives the first 3 weeks after birth, preferably the animal survives the first 4 weeks after birth.

The term 'colostrum', as used herein, refers to the milk secreted between parturition and 24 hours thereafter. Colostrum uptake by the offspring, which typically corresponds to the colostrum production of the pregnant animals, can be calculated based on the increase in body weight of the offspring between birth and 24 hours thereafter, based on the algorithm developed by Theil et al. (Mechanistic model to predict colostrum intake based on deuterium oxide dilution technique data and impact of gestation and prefarrowing diets on piglet intake and sow yield of colostrum. J. Anim. Sci. 2014, 92:5507-5519).

The term 'average daily gain' as used herein refers to a value that shows the average weight gain of an animal per day. It is obtained by dividing how much an animal has grown (weight increase) by the number of days needed to accomplish it.

The term 'sorbic acid' as used herein refers to a compound also known as 2,4-hexadienoic acid, or by chemical formulas $CH_3(CH)_4CO_2H$ or $C_6H_8O_2$. It can for example be used as preservative for foodstuffs, or as an antimicrobial agent against microorganisms, like yeasts and moulds. The term 'sorbic acid or an ester or salt thereof' refers to any ester form or salt form of sorbic acid. Non-limiting examples of sorbic acid ester are sorbic acid methyl ester or sorbic acid venyl ester. Non-limiting examples of sorbic acid salts are potassium sorbate, sodium sorbate or calcium sorbate.

The term 'betaine' as used herein refers to a compound which is a N-trimethylated amino acid in a zwitterionic form at neutral pH. It exists as a naturally occurring nutrient found in sugar beets and other plants. It might also be available as a variant, such as a synthetic variant. It includes all chemical forms, including for example betaine anhydrous and betaine hydrochloride. It is also known as trimethylglycine, glycine betaine, glycine hydrochloride, or by chemical formula $C_5H_{11}NO_2$, in hydrated or anhydrous forms.

The term 'ursolic acid' as used herein refers to a pentacyclic triterpenoid identified in the epicuticular waxes of apples as early as 1920 and widely found in the peels of fruits, as well as in herbs and spices like rosemary and thyme. It has the following molecular structure:

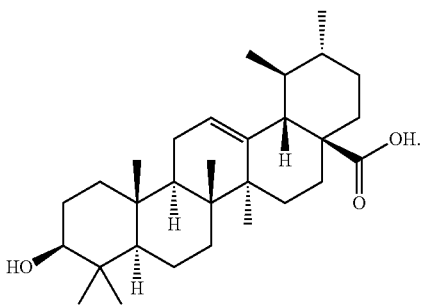

Usually, ursolic acid is extracted from rosemary, from which it can be obtained in purity levels of about 90% or more.

The term 'ursolic acid or an ester or salt thereof' refers to any ester form or salt form of ursolic acid. Non-limiting examples of ursolic acid esters are cis- and trans-3-O-p-hydroxycinnamoyl esters of ursolic acid or ursolic acid alkyl esters like methyl ursolate. Non-limiting examples of ursolic acid salts are sodium ursolate or calcium ursolate.

The term 'diet' as used herein refers to the habitual nourishment of the animal, including feed (solid and liquid feed) and drinking water.

The term 'supplement', also known as 'additive', as used herein refers to a product intended for ingestion, which contains one or more ingredients intended to add nutritional value to the diet. The supplement may be added to a feed composition, and includes, without limitation, animal feeds, top dresses or premixes. It may also be added to the drinking water (in which case the supplement is often referred to as a drinking water additive).

The term lop dress' as used herein refers to an animal feed which is added on the normal diet of the animal. A top dress can be used as a way to add one or more supplements to the diet. Next to the particular one or more supplements, a top dress typically contains materials like barley, wheat, corn, wheat bran, molasses, vegetable oil, and/or sugar.

The term 'premix' as used herein refers to a complex mixture of compounds like vitamins, minerals, trace elements, supplements and/or other nutritional additives, for incorporation into feed. The premix is typically incorporated at a level of between 0.2 and 2% (micro premix) or between 2 to 8% (macro premix) into the feed. It is usually mixed with feed in an early stage in the manufacturing and distribution process.

The terms 'to improve' or 'improving' as used herein refer to the ability to bring in a more desirable state or condition. Someone or something might for example become better or might get better properties or quality. The ability to make things better is also covered in a sense of the ability to ameliorate, like improving a bad situation or quality, or repairing bad or not working properties.

The terms 'to increase' and 'increased level' and the terms 'to decrease' and 'decreased level' refer to the ability to increase or decrease a particular amount or number. A level in a test sample may be increased or decreased when it is at least 5%, such as 10%, 15%, 20%, 25%, 30%, 35%, 40%, 45%, 50% higher or lower, respectively, than the corresponding level in a control sample or reference sample.

The term 'about', as used herein indicates a range of normal tolerance in the art, for example within 2 standard deviations of the mean. The term "about" can be understood as encompassing values that deviate at most 10%, 9%, 8%, 7%, 6%, 5%, 4%, 3%, 2%, 1%, 0.5%, 0.1%, 0.05%, or 0.01% of the indicated value.

The terms "comprising" or "to comprise" and their conjugations, as used herein, refer to a situation wherein said terms are used in their non-limiting sense to mean that items following the word are included, but items not specifically mentioned are not excluded. It also encompasses the more limiting verb "to consist essentially of" and "to consist of".

Reference to an element by the indefinite article "a" or "an" does not exclude the possibility that more than one of the elements is present, unless the context clearly requires that there be one and only one of the elements. The indefinite article "a" or "an" thus usually means "at least one".

Compositions

The present inventor surprisingly found that use of a composition comprising sorbic acid or an ester or salt thereof and betaine, in a diet for a pregnant animal, preferably a sow, increased colostrum production by such sow, increased average daily gain of the offspring and improved neonatal survival of the offspring.

In a first aspect the present invention relates to a method of feeding a pregnant animal, comprising administering a composition comprising sorbic acid or an ester or salt thereof and betaine to the pregnant animal, wherein the dosage of sorbic acid or an ester or salt thereof is in a range of 0.02-100 grams per day, and the dosage of betaine is in a range of 0.02-100 grams per day. Preferably, the dosage of sorbic acid or an ester or salt thereof is in a range of 0.1-50 grams per day, more preferably in a range of 0.5-20 grams per day, more preferably in a range of 2-8 grams per day, more preferably in a range of 3-7 grams per day, more preferably in a range of 4-6 grams per day. The dosage of betaine is preferably in a range of 0.1-50 grams per day, more preferably in a range of 0.7-20 grams per day, more preferably in a range of 1-5 grams per day, more preferably in a range of 2-4 grams per day. In an embodiment, the composition further comprises ursolic acid or an ester or salt thereof, wherein the dosage is in a range of 0.02-100 grams per day. Preferably, the dosage of ursolic acid or an ester or salt thereof is in a range of 0.05-50 grams per day, more preferably in a range of 0.07-20 grams per day, more preferably in a range of 0.09-10 grams per day, more preferably in a range of 0.1-4 grams per day, even more preferably in a range of 0.2-2 grams per day.

The pregnant animal is preferably a pregnant mammal, more preferably a pregnant monogastric mammal, even more preferably a pregnant sow. It is not relevant in which form the composition is added to the diet as long as the animal receives the necessary daily dose of sorbic acid or an ester or salt thereof and betaine. Pregnant sows for example eat about 2.5 to 3.5 kg feed a day and drink about 7 liters of drinking water a day. This means that the amount of sorbic acid or an ester or salt thereof and betaine to be added either to the feed, or to the drinking water, or to both the feed and drinking water, can easily be determined in order to result in the necessary daily dose of the invention.

In an aspect, the present invention relates to an animal feed, comprising sorbic acid or an ester or salt thereof and betaine, wherein the dosage of sorbic acid or an ester or salt thereof is in a range of 0.02-100 grams per kilogram animal feed, and the dosage of betaine is in a range of 0.02-100 grams per kilogram animal feed. Preferably, the dosage of sorbic acid or an ester or salt thereof is in a range of 0.1-70 grams per kilogram animal feed, more preferably in a range of 0.5-40 grams per kilogram feed, more preferably in a range of 1-10 grams per kilogram feed, more preferably in a range of 1.2-4 grams per kilogram feed, more preferably in a range of 1.4-2 grams per kilogram feed. The dosage of betaine is preferably in a range of 0.1-70 grams per kilogram feed, more preferably in a range of 0.3-40 grams per kilogram feed, more preferably in a range of 0.5-10 grams per kilogram feed, more preferably in a range of 0.6-3, more preferably in a range of 0.7-2, more preferably in a range of 0.8-1.4. In an embodiment, the animal feed further comprises ursolic acid or an ester or salt thereof, wherein the dosage is in a range of 0.02-100 grams per kilogram animal feed. Preferably, the dosage of ursolic acid or an ester or salt thereof is in a range of 0.04-50 grams per kg animal feed, more preferably in a range of 0.06-20 grams per kg animal feed, more preferably in a range of 0.08-5 grams per kg animal feed, more preferably in a range of 0.09-2 grams per kg animal feed, even more preferably in a range of 0.1-1 grams per kg animal feed.

It is known to the person skilled in the art that animal feed can be formulated in many different ways, which means supplements can be added to the feed in different ways.

In an embodiment, the composition as taught herein is added to an animal feed as a top dress formulation. Top dresses are typically added to the feed in a certain amount per kilogram feed. A non-limiting example is the addition of 100 grams of top dress to 1 kg of feed. In that case, for a dosage of 0.5 gram betaine per kg of feed, 100 grams of top dress should contain 5 grams of betaine in order to formulate the necessary dose per kilogram feed. When in another non-limiting example feed is formulated containing 1.2 grams of betaine per kilogram feed, by the use of 50 grams of a top dress formulation per kilogram of feed, the top dress formulation should contain 24 grams of betaine in 50 grams of top dress.

The top dress may comprise one or more additional components in addition to the composition as taught herein. These one or more additional components may serve as a carrier material for the composition as taught herein. Non-limiting examples of the one or more additional components are barley, wheat, corn, wheat bran, molasses, vegetable oil, sugar, chalk and the like. In an embodiment, the top dress comprises the composition as taught herein without one or more additional components. In an embodiment the top dress comprises the composition as taught herein, wherein the dosage of the composition is 0.5-100%, based on the total weight of the said top dress, preferably the dosage of the composition is 1-75%, based on the total weight of the said top dress, more preferably the dosage of the composition is 2-50%, based on the total weight of the said top dress, more preferably the dosage of the composition is 3-30%, based on the total weight of the said top dress, even more preferably the dosage of the composition is 5-20%, based on the total weight of the said top dress, most preferably the dosage of the composition is 7-15%, based on the total weight of the said top dress. In an embodiment, the top dress comprises the composition as taught herein, wherein the dosage of the said composition is intended to provide dosages in a range of 0.02-100 g sorbic acid or an ester or salt thereof per day, 0.02-100 g betaine per day, and optionally 0.02-100 g ursolic acid or an ester or salt thereof per day. Preferably, the dosage of sorbic acid or an ester or salt thereof is in a range of 0.1-50 grams per day, more preferably in a range of 0.5-20 grams per day, more preferably in a range of 2-8 grams per day, more preferably in a range of 3-7 grams per day, more preferably in a range of 4-6 grams per day. The dosage of betaine is preferably in a range of 0.1-50 grams per day, more preferably in a range of 0.7-20 grams per day, more preferably in a range of 1-5 grams per day, more preferably in a range of 2-4 grams per day. The dosage of ursolic acid or an ester or salt thereof is preferably in a range of 0.02-100 grams per day, more preferably in a range of 0.05-50 grams per day, more preferably in a range of 0.07-20 grams per day, more preferably in a range of 0.09-10 grams per day, more preferably in a range of 0.1-4 grams per day, even more preferably in a range of 0.2-2 grams per day.

Alternatively, the composition as taught herein may be added to an animal feed by direct addition of the composition in the feed formulation process, or by the use of a supplement or premix. A premix, which is a complex mixture of compounds, may be incorporated in feed in certain percentages during the feed formulation process. The percentages of incorporation can vary from one feed to the other. A non-limiting example is a feed comprising 1 gram betaine per kg feed, formulated by addition of 1% of premix into the animal feed. In case of 1% incorporation, the premix should contain 100 grams of betaine for 1 kilogram of premix, in order to end up with a dosage of 1 gram of betaine per kilogram feed.

The supplement or premix may comprise one or more additional components in addition to the composition as taught herein. These one or more additional components may serve as a carrier material for the composition as taught herein. Non-limiting example of the one or more additional components are vitamins, minerals, trace elements, supplements, other nutritional additives, chalk and the like. In an embodiment, the supplement or premix comprises the composition as taught herein without one or more additional components. In an embodiment the supplement or premix comprises the composition as taught herein, wherein the dosage of the composition is 5-100%, based on the total weight of the said supplement or premix, preferably the dosage of the composition is 3-90%, based on the total weight of the said supplement or premix, more preferably the dosage of the composition is 6-80%, based on the total weight of the said supplement or premix, more preferably the dosage of the composition is 9-70%, based on the total weight of the said supplement or premix, even more preferably the dosage of the composition is 15-60%, based on the total weight of the said supplement or premix, most preferably the dosage of the composition is 20-45%, based on the total weight of the said supplement or premix. In an embodiment, the supplement or premix comprises the composition as taught herein, wherein the dosage of the said composition is intended to provide dosages in a range of 0.02-100 g sorbic acid or an ester or salt thereof per day, 0.02-100 g betaine per day, and optionally 0.02-100 g ursolic acid or an ester or salt thereof per day. Preferably, the dosage of sorbic acid or an ester or salt thereof is in a range of 0.1-50 grams per day, more preferably in a range of 0.5-20 grams per day, more preferably in a range of 2-8 grams per day, more preferably in a range of 3-7 grams per day, more preferably in a range of 4-6 grams per day. The dosage of betaine is preferably in a range of 0.1-50 grams per day, more preferably in a range of 0.7-20 grams per day, more preferably in a range of 1-5 grams per day, more preferably in a range of 2-4 grams per day. The dosage of ursolic acid or an ester or salt thereof is preferably in a range of 0.02-100 grams per day, more preferably in a range of 0.05-50 grams per day, more preferably in a range of 0.07-20 grams per day, more preferably in a range of 0.09-10 grams per day, more preferably in a range of 0.1-4 grams per day, even more preferably in a range of 0.2-2 grams per day.

In a further aspect the invention relates to an animal drinking water, comprising sorbic acid or an ester or salt thereof and betaine, wherein the dosage of sorbic acid or an ester or salt thereof is in a range of 0.02-100 grams per liter animal drinking water, and the dosage of betaine is in a range of 0.02-100 grams per liter animal drinking water. Preferably, the dosage of sorbic acid or an ester or salt thereof is in a range of 0.1-50 grams per liter animal drinking water, more preferably in a range of 0.4-20 grams per liter drinking water, more preferably in a range of 0.7-4 grams per liter drinking water, more preferably in a range of 0.8-3 grams per liter drinking water, more preferably in a range of 0.9-2 grams per liter drinking water. The dosage of betaine is preferably in a range of 0.07-50 grams per liter animal drinking water, more preferably in a range of 0.1-20 grams per liter drinking water, more preferably in a range of 0.2-4 grams per liter drinking water, more preferably in a range of 0.3-2 grams per liter drinking water, more preferably in a range of 0.4-1 grams per liter drinking water. In an embodiment, the animal drinking water further comprises ursolic acid or an ester or salt thereof, wherein the dosage is in a range of 0.01-100 grams per liter animal drinking water. Preferably, the dosage of ursolic acid or an ester or salt thereof is in a range of 0.01-50 grams per liter animal drinking water, more preferably in a range of 0.02-20 grams per liter animal drinking water, more preferably in a range of 0.02-5 grams per liter animal drinking water, more preferably in a range of 0.03-2 grams per liter animal drinking water, even more preferably in a range of 0.03-1 gram per liter animal drinking water.

In an embodiment, the composition as taught herein may be added to the diet of animals by adding part of the daily dose to the animal feed and the other part of the daily dose to the drinking water. It is known to the skilled person that, in an embodiment, such a diet can be formulated by addition of one part, comprising sorbic acid or an ester or salt thereof and betaine, to the feed and the other part, comprising sorbic acid or an ester or salt thereof and betaine, to the drinking water. In another embodiment one part, e.g., comprising the sorbic acid or an ester or salt thereof, is added to the feed and another part, e.g., comprising betaine, is added to the drinking water. In another embodiment, one part, e.g., comprising sorbic acid or an ester or salt thereof, is added to the drinking water and another part, e.g., comprising betaine, is added to the feed. In an embodiment, a diet can be formulated by addition of one or two parts, selected from sorbic acid or an ester or salt thereof or betaine or ursolic acid or an ester or salt thereof, to the feed; and one or two parts, selected from sorbic acid or an ester or salt thereof, or betaine or ursolic acid or an ester or salt thereof, to the drinking water, in order to end up with a diet comprising three parts, one part being sorbic acid or an ester or salt thereof, one part being betaine, and one part being ursolic acid or an ester or salt thereof, spread over the animal feed and/or the drinking water.

In an aspect, the invention relates to a method of producing the composition as taught herein, said method comprising the steps of mixing sorbic acid or an ester or salt thereof and betaine, with one or more feed components or one or more feed additives or water, to produce the animal feed or drinking water taught herein, wherein the amount of sorbic acid or an ester or salt thereof in the composition is intended to provide a dosage in a range of 0.02-100 grams per day, and the amount of betaine in the composition is intended to provide a dosage in a range of 0.02-100 grams per day. In an embodiment, the invention relates to a method of producing the composition as taught herein, said method comprising the steps of mixing sorbic acid or an ester or salt thereof and betaine and ursolic acid or an ester or salt thereof, with one or more feed components or one or more feed additives or water, to produce the animal feed or drinking water taught herein, wherein the amount of sorbic acid or an ester or salt thereof in the composition is intended to provide a dosage in a range of 0.02-100 grams per day, the amount of betaine in the composition is intended to provide a dosage in a range of 0.02-100 grams per day, and the amount of ursolic acid or an ester or salt thereof is intended to provide a dosage in a range of 0.02-100 grams per day. Compositions as taught herein are preferably essentially free of inulin.

Methods and Uses of the Composition

In an aspect the invention relates to a method of feeding a pregnant animal, preferably a sow, or a method of producing a composition as taught herein for a pregnant animal, preferably a sow, wherein the composition is selected from a group consisting of a top dress formulation, an animal feed, a premix, a supplement, and an animal drinking water.

In an embodiment, the composition as taught herein is administered to the pregnant animal, preferably a pregnant sow, in a period from about 45 days prior to parturition until parturition. In an embodiment, the composition as taught herein is administered to the pregnant animal, preferably a pregnant sow, in a period from about 40 days prior to parturition until parturition. In an embodiment, the composition as taught herein is administered to the pregnant animal, preferably a pregnant sow, in a period from about 35 days prior to parturition until parturition.

In an aspect, the invention relates to the use of a composition as taught herein in a diet for a pregnant animal, preferably a sow. The inventor surprisingly found that a composition as taught herein can be used for non-medical as well as medical purposes.

In another aspect, the invention relates to use of a composition comprising sorbic acid or an ester or salt thereof and betaine, particularly a composition as taught herein, for increasing the colostrum production. It is known to the person skilled in the art that the offspring consumes more colostrum if more colostrum is available to the newborn animals. A higher colostrum uptake by the litter therefore means that more colostrum was produced by the pregnant animal.

In a further aspect, the invention relates to use of a composition comprising sorbic acid or an ester or salt thereof and betaine, particularly a composition as taught herein, for increasing average daily gain of the offspring.

In a further aspect, the invention relates to use of a composition comprising sorbic acid or an ester or salt thereof and betaine, particular a composition as taught herein, for use in improving neonatal survival of the offspring.

In a further aspect, the composition taught herein may be administered to the animal for enhancing mammary gland development.

In a further aspect, the composition taught herein may be administered to the animal for increasing mammary gland tissue mass.

In an embodiment, the composition taught herein, is administered to the animal only during gestation, preferably in a period from about 45 days prior to parturition up to parturition, more preferably in a period from about 40 days prior to parturition until parturition, more preferably in a period from about 35 days prior to parturition until parturition. In an embodiment, the composition taught herein is selected from a group consisting of a top dress formulation, an animal feed, a premix, a supplement, and an animal drinking water.

The present invention is further illustrated, but not limited, by the following examples. From the above discussion and the examples, one skilled in the art can ascertain the essential characteristics of the present invention, and without departing from the teaching and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

EXAMPLES

Example 1

From day 80 of gestation up to parturition (day 115 of gestation), sows of various parities were fed a top dress of 100 g/day on top of a normal gestation diet, comprising sorbic acid alone, betaine alone, or neither of the two as a control. The dosages are specified in Table 1.

TABLE 1

| Ingredient | Daily dose in 100 g top dress | In total diet (3 kg feed), g/kg |
|---|---|---|
| Sorbic acid | 5 g | 1.67 |
| Betaine | 3 g | 1.00 |

Parities were equally distributed across treatments (control, betaine, sorbic acid). The normal diet was fed at approximately 3 kg/day. Other than the active compounds, the top dress was formulated from barley, wheat, corn, wheat bran, molasses, vegetable oil, and sugar. At parturition, piglets were weighed immediately as they were born, and again at 24 h after birth, to estimate colostrum intake based on the algorithm developed by Theil et al. (*Mechanistic model to predict colostrum intake based on deuterium oxide dilution technique data and impact of gestation and prefarrowing diets on piglet intake and sow yield of colostrum. J. Anim. Sci.* 2014, 92:5507-5519). Colostrum intake per litter was slightly lower for the sorbic acid treatment compared to the control. For betaine, total colostrum intake per litter was substantially lower than the control. Looking at the average daily gain to day 7, the sorbic acid treatment showed the same result as the control. The betaine treatment showed a negative effect on average daily gain compared to the control treatment (Table 2).

TABLE 2

| Ingredient | Number of animals | Daily dose in 100 g top dress | Total colostrum intake per litter*, g | Average daily gain to day 7, kg per litter* |
|---|---|---|---|---|
| Control | 20 | | 6342 | 18.2 |
| Sorbic acid | 16 | 5 g | 6227 | 18.2 |
| Betaine | 15 | 3 g | 5784 | 16.1 |

*corrected for litter size.

Example 2

From day 80 of gestation up to parturition, sows of various parities were fed a top dress of 100 g/day on top of a normal gestation diet, which additionally contained a combination of active compounds as specified in Table 3, or not (control). Dosage of sorbic acid and betaine were the same as in Study 1 and specified in Table 1. Parities were equally distributed across treatments. The normal diet was fed at approximately 3 kg/day. At parturition, piglets were weighed immediately as they were born, and again at 24 h after birth, to estimate colostrum intake based on the algorithm developed by Theil et al. (*Mechanistic model to predict colostrum intake based on deuterium oxide dilution technique data and impact of gestation and prefarrowing diets on piglet intake and sow yield of colostrum. J. Anim. Sci.* 2014, 92:5507-5519). Piglets were assessed and weighed again at day 7 after birth to determine neonatal survival and weight gain in this period.

Colostrum intake per litter was increased by the treatment combination containing sorbic acid and betaine (Table 3). Neonatal survival was improved by the combination of sorbic acid and betaine. Also an increase in average daily gain was found as an effect of treatment with sorbic acid and betaine.

TABLE 3

| Ingredient Combinations** | Number of animals | Total colostrum intake per litter*, g | Neonatal mortality to day 7 after birth | Average daily gain to day 7, kg per litter* |
|---|---|---|---|---|
| Control | 18 | 5073 | 12.2% | 15.9 |
| Sorbic acid + Betaine | 17 | 5574 | 4.4% | 16.5 |

*corrected for litter size.
**Sorbic acid was supplemented at 5 g/d, betaine at 3 g/d.

Example 3

From day 80 of gestation up to parturition, sows of various parities were fed a top dress of 100 g/day on top of a normal gestation diet, which additionally contained a combination of active compounds as specified in Table 4, or not (control). Dosage of compounds betaine and sorbic acid were the same as in Study 1 and specified in Table 1. In additional treatments, ursolic acid was added as a third compound on top of betaine and sorbic acid, as specified in Table 4. Ursolic acid was provided at 0.3 g/d and at 0.6 g/d in the respective treatments. Parities were equally distributed across treatments. The normal diet was fed at approximately 3 kg/day. At parturition, piglets were weighed immediately as they were born, and again at 24 h after birth, to estimate colostrum intake based on the algorithm developed by Theil et al. (*Mechanistic model to predict colostrum intake based on deuterium oxide dilution technique data and impact of gestation and prefarrowing diets on piglet intake and sow yield of colostrum. J. Anim. Sci.* 2014, 92:5507-5519). Number of piglets was assessed at day 7 after birth to determine neonatal survival. Piglets were then assessed and weighed again at day 24 (end of lactation period), to determine litter gain to weaning and pre-wean mortality.

Colostrum intake per litter was increased by the treatment combinations vs. the control treatment (Table 4). Neonatal survival (to day 7) was improved by the combination of sorbic acid and betaine. Also an increase in average daily gain (to day 24) was found as an effect of treatment with sorbic acid and betaine. The addition of ursolic acid had a surprising improved effect compared to only betaine and sorbic acid. Neonatal and pre-wean survival were further improved and the litter gain to wean (day 1-24) was also increased further when adding ursolic acid to the combination of betaine and sorbic acid. Because of improved neonatal and pre-wean survival due to addition of ursolic acid, litter size at weaning was also improved.

TABLE 4

| Ingredient combinations | Number of animals | Total colostrum intake per litter‡, g | Neonatal mortality to day 7 after birth | Pre-wean mortality to day 24 after birth | Average dailay gain to day 24, kg per litter‡‡ |
|---|---|---|---|---|---|
| Control | 49 | 5393 | 10.5% | 12.6% | 66.5 |
| Sorbic acid + Betaine | 33 | 5768 | 9.1% | 10.6% | 67.5 |
| Sorbic acid + Betaine + 0.3 g/d ursolic acid | 36 | 5753 | 8.3% | 9.5% | 69.1 |
| Sorbic acid + Betaine + 0.6 g/d ursolic acid | 16 | 5693 | 7.0% | 8.1% | 67.9 |

‡Corrected for number of liveborn;
‡‡Corrected for litter size at the start of lactation

The invention claimed is:

1. An animal feed, comprising (a) sorbic acid or an ester or salt thereof and (b) betaine.

2. The animal feed according to claim 1, comprising 0.02-100 grams per kilogram animal feed of the sorbic acid or an ester or salt, and 0.02-100 grams per kilogram animal feed of the betaine.

3. The animal feed according to claim 1, further comprising (c) ursolic acid or an ester or salt thereof.

4. The animal feed according to claim 3, comprising 0.02-100 grams per kilogram animal feed of ursolic acid or an ester or salt thereof.

5. The animal feed according to claim 1, in the form of a top dress formulation, an animal feed, a premix or supplement or an animal drinking water.

6. An animal drinking water, comprising (a) 0.02-100 grams per liter animal drinking water of sorbic acid or an ester or salt thereof, and (b) 0.02-100 grams per liter animal drinking water of betaine.

7. The animal drinking water according to claim 6, further comprising ursolic acid or an ester or salt thereof.

8. The animal drinking water according to claim 7, comprising 0.01-100 grams per liter animal drinking water of ursolic acid or an ester or salt thereof.

9. A method of feeding a pregnant mammal, comprising administering to the mammal 0.02-100 grams per day sorbic acid or an ester or salt thereof and 0.02-100 grams per day betaine.

10. The method according to claim 9, further comprising administering to the mammal ursolic acid or an ester or salt thereof.

11. The method according to claim 10, comprising administering 0.02-100 grams per day ursolic acid or an ester or salt thereof.

12. The method according to claim 9, wherein the mammal is a monogastric mammal.

13. The method according to claim 12, wherein the monogastric mammal is a sow.

14. The method according to claim 9, wherein the composition is administered to the pregnant mammal in a period from about 45 days prior to parturition until parturition.

15. The method according to claim 14, wherein the composition is administered to the pregnant mammal in a period from about 40 days prior to parturition until parturition.

16. The method according to claim 15, wherein the composition is administered to the pregnant mammal in a period from about 35 days prior to parturition until parturition.

17. A method for increasing colostrum production, comprising administering to the mammal in need thereof an animal feed according to claim 1.

18. A method for increasing average daily gain of offspring of a mammal, comprising administering to the mammal in need thereof an animal feed according to claim 1.

19. A method for improving neonatal survival of offspring of a mammal, comprising administering to the mammal in need thereof an animal feed according to claim 1.

20. A method for increasing the number of offspring of a mammal that reach the age of three weeks, comprising administering to the mammal in need thereof an animal feed according to claim 1.

21. A method of producing an animal feed composition for a pregnant mammal, comprising mixing:
   (a) 0.02-100 grams per kilogram animal feed of sorbic acid or an ester or salt thereof,
   (b) 0.02-100 grams per kilogram animal feed of betaine, and
   (c) one or more feed components or one or more feed additives or water.

* * * * *